(12) United States Patent
Markham

(10) Patent No.: US 8,372,387 B2
(45) Date of Patent: Feb. 12, 2013

(54) COMPOSITIONS AND METHODS FOR THE TREATMENT OF HEART FAILURE

(75) Inventor: Bruce Edward Markham, Novi, MI (US)

(73) Assignee: Phrixus Pharmaceuticals, Inc., Ann Arbor, MI (US)

( * ) Notice: Subject to any disclaimer, the term of this patent is extended or adjusted under 35 U.S.C. 154(b) by 280 days.

(21) Appl. No.: 12/593,798

(22) PCT Filed: Apr. 4, 2008

(86) PCT No.: PCT/US2008/004437
§ 371 (c)(1), (2), (4) Date: Feb. 17, 2010

(87) PCT Pub. No.: WO2008/124088
PCT Pub. Date: Oct. 16, 2008

(65) Prior Publication Data
US 2010/0178269 A1 Jul. 15, 2010

Related U.S. Application Data

(60) Provisional application No. 60/922,047, filed on Apr. 5, 2007.

(51) Int. Cl.
*A61K 31/74* (2006.01)
*A61K 31/765* (2006.01)

(52) U.S. Cl. .................... 424/78.31; 424/78.37

(58) Field of Classification Search ............. 424/78.31, 424/78.37
See application file for complete search history.

(56) References Cited

U.S. PATENT DOCUMENTS

| | | | |
|---|---|---|---|
| 5,198,211 | A | 3/1993 | Hunter et al. |
| 5,605,687 | A | 2/1997 | Lee |
| 6,342,247 | B1 | 1/2002 | Ku et al. |
| 6,747,064 | B2 | 6/2004 | Emanuele et al. |
| 6,761,824 | B2 | 7/2004 | Reeve et al. |
| 6,977,045 | B2 | 12/2005 | Reeve et al. |
| 7,846,426 | B2 | 12/2010 | Metzger et al. |
| 2006/0121016 | A1 | 6/2006 | Lee |
| 2007/0237740 | A1 | 10/2007 | Reddington et al. |
| 2008/0260681 | A1* | 10/2008 | Metzger et al. ............ 424/78.38 |
| 2009/0246162 | A1* | 10/2009 | Markham ................. 424/78.3 |
| 2010/0178269 | A1 | 7/2010 | Markham |

FOREIGN PATENT DOCUMENTS

| | | |
|---|---|---|
| WO | WO 92/22202 | 12/1992 |
| WO | WO 00/21543 | 4/2000 |
| WO | WO 02/065834 | 8/2002 |
| WO | WO 2006/037031 | 4/2006 |
| WO | WO 2006/091941 | 8/2006 |
| WO | WO2006/091941 | * 8/2006 |
| WO | WO 2008/016640 | 2/2008 |
| WO | WO2008/016640 | * 2/2008 |
| WO | WO 2008/124088 | 10/2008 |
| WO | WO 2009/078978 | 6/2009 |
| WO | WO 2009/079562 | 6/2009 |

OTHER PUBLICATIONS

Alexaner Justicz, et al, Reduction of Myocardial Infarct Size by Poloxamer 188 and Manitol in a Canine Model, 122 Am. Heart J 671 (1991).*
Alexander Justicz, et al, Reduction of Myocardial Infarct Size by Poloxamer 188 and Mannitol in a Canine Model, 122 Am. Heart J 671 (Sep. 1991).*
Ochi, Rikuo, et al. "Electroporation of cardiac muscle: modulation by lysolipids, surfactants and polyethylene glycol", Jpn. J. Electrocardiology, vol. 20, Supp. 3, pp. S-3-20-S-3-23, 2000.
Watanabe, Makino, et al., "Lysophosphatidylcholine-induced myocardial damage is inhibited by pretreatment with poloxamer 188 in isolated rat heart", Molecular and Cellular Biochemistry, vol. 248, 2003, pp. 209-215.
Adams-Graves, Patricia, et al., "RheothRx (Poloxamer 118) Injection for the Acute Painful Episode of Sickle Cell Disease: A Pilot Study", Blood, 1997, vol. 90, No. 5, pp. 2041-2046.
Angeja, Brad G., et al., "Evaluation and Management of Diastolic Heart Failure" Circulation, 2003, vol. 107, pp. 659-663.
Baczko, Istvan, et al., "Pharmacological activation of plasma-membrane KATP channels reduces reoxygenation-induced Ca2+ overload in cardiac myocytes via modulation of the diastolic membrane potential", British Journal of Pharmacology, Mar. 2004, vol. 141, No. 6, pp. 1059-1067.
Balghith, Mohammed, et al., "Assessment of diastolic dysfunction after acute myocardial infarction using Doppler echocardiography", Canadian Journal Cardiology, Jan. 2002, vol. 18, No. 1, pp. 69-77.
Blake, Derek J., et al., "Function and Genetics of Dystrophin and Dystrophin-Related Proteins in Muscle", Physiol Rev, Apr. 2002, vol. 82, pp. 291-329.
Borgens, Richard B., et al., "Subcutaneous Tri-Block Copolymer Produces Recovery From Spinal Cord Injury", Journal of Neuroscience Research, 2004, vol. 76, pp. 141-154.
Bulfield, Grahame, et al., "X chromosome-linked muscular dystrophy (mdx) in the mouse", Proc. Natl. Acad. Sci. USA, 1984, vol. 81, pp. 1189-1192.
Chareonthaitawee, P., et al., "The impact of time to thrombolytic treatment on outcome in patients with acute myocardial infarction", Heart, 2000, vol. 84, pp. 142-148.
Emanuele, R. Martin, et al., "FLOCOR: a new anti-adhesive, rheologic agent.", Expert Opin Investig Drugs, 1998, vol. 7, No. 7, pp. 1193-1200.

(Continued)

*Primary Examiner* — Sean Basquill
(74) *Attorney, Agent, or Firm* — Honigman Miller Schwartz and Cohn LLP; Jonathan P. O'Brien; David J. Johnson

(57) ABSTRACT

The invention provides a therapeutic composition comprising an aqueous buffer, and a therapeutic agent that improves the functioning of a diseased heart by decreasing left ventricular end-diastolic pressure and simultaneously increasing left ventricular ejection without affecting the blood pressure or heart rate.

14 Claims, 6 Drawing Sheets

OTHER PUBLICATIONS

Finstere, Josef, et al., "The Heart in Human Dystophinopathies", Cardiology, vol. 99, No. 1, pp. 1-19, 2003.

Gibbs, Winter J., et al., "Purified Poloxamer 188 for Sickle Cell Vaso-Occlusive Crisis", The Annals of Pharmacotherapy, Feb. 2004, vol. 38, No. 2, pp. 320-324.

Goyenvalle, Aurélie, et al., "Rescue of Dystrophic Muscle Through U7 snRNA-mediated Exon Skipping", Science, 2004, vol. 306, pp. 1796-1799.

Gregorevic, Paul, et al., "Systemic delivery of genes to strained muscles using adeno-associated viral vectors", Nature Medicine, Aug. 2004, vol. 10, No. 8, pp. 828-834.

Grover, Frederick L., et al., "Effect of a Nonionic Surface-Active Agent on Blood Viscosity and Platelet Adhesiveness", Circulation, 1969, vol. 39, I-1249.

Halacheva, Silvia, et al., "Poly(glycidol)-Based Analogues to Pluronic Block Copolymers. Synthesis and Aqueous Solution Properties", Macromolecules, 2006, vol. 39, pp. 6845-6852.

Head, Stewart I., et al., "Abnormalities in structure and function of limb skeletal muscle fibers or dystrophy mdx mice", Proceedings: Biological Sciences, May 22, 1992, vol. 248, No. 1322, pp. 163-169.

Hoffman, Eric P., et al., "Dystrophin: The Protein Product of the Duchenne Muscular Dystrophy Locus", Cell, 1987, vol. 51, pp. 919-928.

Hunt, Sharon A., et al., "ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure)", Circulation, 2001, vol. 104, pp. 2996-3007.

Kabanov, Alexander V., et al., "Pluronic block copolymers for overcoming drug resistance in cancer", Advanced Drug Delivery Reviews, 2002, vol. 54, pp. 758-779.

Kainthan, Rajesh Kumar, et al., "Biocompatibility Testing of Branched and Linear Polyglycidol", Biomacromolecules, Mar. 2006, vol. 7, No. 3, pp. 703-709.

Kaprielian, Raffi R., et al., "Dystrophin and the cardiomyocyte membrane cytoskeleton in the healthy and failing heart", Heart Failure Reviews, 2000, vol. 5, pp. 221-238.

Kawada, Tomie, et al., "A novel paradigm for the therapeutic basis of advanced heart failure-assessment by gene therapy", Pharmacology & Therapeutics, 2005, vol. 107, pp. 31-43.

Lamb, G. D., et al., "Raised intracellular [Ca2+] abolishes excitation-contraction coupling in skeletal muscle fibers of rat and toad", Journal of Physiology, 1985, vol. 489, No. 2, pp. 349-362.

Lee, Raphael C., et al., "Pharmaceutical therapies for sealing of premeabilized cell membranes in electrical injuries", Annals New York Academy of Sciences, 1999, vol. 888, pp. 266-273.

Lee, Raphael C., et al., "Surfactant-induced sealing of electropermeabilizied skeletal muscle membranes in vivo", Proc. Natl. Acad. Sci. USA, 1992, vol. 89, pp. 4524-4528.

Li, Sheng, et al., "A highly functional mini-dystrophin/GFP fusion gene for cell and gene therapy studies of Duchenne muscular dystrophy", Human Molecular Genetics, 2006, vol. 15, No. 10, pp. 1610-1622.

Liang, Qiangrong, et al., "Redefining the roles of p38 and JNK signaling in cardiac hypertrophy: dichotomy between cultured myocytes and animal models", Journal of Molecular and Cellular Cardiology, 2003, vol. 35, pp. 1385-1394.

Lynch, Gordon S., et al., "Force and power output of fast and slow skeletal muscles from mdx mice 6-28 months old", Journal of Physiology, 2001, vol. 535, No. 2, pp. 591-600.

Marks, Jeremy D., et al., "Amphiphillic, tri-block copolymers provide potent, membrane-targeted neuroprotection", The FASEB Journal, 2001, vol. 15, pp. 1107-1109.

Maskarinec, Stacey A., et al., "Direct Observation of Poloxamer 188 Insertion into Lipid Monolayers", Biophysical Journal, Mar. 2002, vol. 82, pp. 1453-1459.

Maynard, Charles, et al., "Randomized, controlled trial of RheothRx (poloxamer 188) in patients with suspected acute myocardial infarction", American Heart Journal, May 1, 1998, vol. 135, No. 5, pp. 797-804.

Merchant, F. A., et al., "Poloxamer 188 Enhances Functional Recovery of Lethally Heat-Shocked Fibroblasts", Journal of Surgical Research, 1998, vol. 74, pp. 131-140.

Michele, Daniel E., et al., "Cardiac Dysfunction in Hypertrophic Cardiomyopathy Mutant Tropomyosin Mice is Transgene-Dependant, Hypertrophy-Independent, and Improved by β-Blockade", Circulation Research, 2002, vol. 91, pp. 255-262.

Modi, Nishit B., "Flocor CytRx Corp", IDrugs, 1999, vol. 2, No. 4, pp. 366-374.

Mutoni, Francesco, "Cardiomyopathy in muscular dystrophies", Current Opinion in Neurology, 2003, vol. 16, pp. 577-583.

Myocardial Preconditioning, Specialty: Myocardial Ischemia/Function/Metabolism, Monday Afternoon, Earnest N Morial Convention Center, 286-287, Abstracts 641-650, 2004.

Ohlendieck, Kay, et al., "Dystrophin-associated Proteins Are Greatly Reduced in Skeletal Muscle From mdx Mice", Journal of Cell Biology, Dec. 1991, vol. 115, No. 6, pp. 1685-1694.

O'Keefe, James H., Jr., et al., "Poloxamer-188 as an Adjunct to Primary Percutaneous Transluminal Coronary Angioplasty for Acute Myocardial Infarction", American Journal of Cardiology, Oct. 1, 1996, vol. 78, pp. 747-750.

Pasternak, Carmela, et al., "Mechanical Function of Dystrophin in Muscle Cells", The Journal of Cell Biology, Feb. 1995, vol. 128, No. 3, pp. 355-361.

Petrof, Basil J., "Molecular Pathophysiology of Myofiber Injury in Deficiencies of the Dystrophin-Glycoprotein Complex", American Journal of Physical Medicine & Rehabilitation, Nov. 2002, vol. 81, No. 11, pp. S162-S174.

Raev, Dimitar C., "Which Left Ventricular Function Is Impaired Earlier in the Evolution of Diabetic Cardiomyopathy? An echocardiographic study of young type I diabetic patients", Diabetes Care, Jul. 1994, vol. 17, No. 7, pp. 633-639.

Reeve, Loraine E., "The Poloxamers: Their Chemistry and Medical Application", In: Handbook of Biodegradable Polymers, Harwood Academic Pub, 1997, pp. 231-249.

Schaer, Gary L., et al., "Beneficial effects of RheothRx injection in patients receiving thrombolytic therapy for acute myocardial infarction. Results of a randomized, double-blind, placebo-controlled trial", Circulation, Aug. 1996, vol. 94, No. 3, pp. 298-370.

Schmolka, Irving R., "A Review of Block Polymer Surfactants", Journal of the American Oil Chemists' Society, Mar. 1977, vol. 54, pp. 110-116.

Shibata, Marcelo, et al., "Study of the Effects of Nebivolol Intervention on Outcomes and Rehospitalization in Seniors with Heart Failure (Seniors). Rational and design", International Journal of Cardiology, 2002, vol. 86, pp. 77-85.

Sokabe, Masahiro, et al., "Blockers and Activators for Stretch-Activated Ion Channels of Chick Skeletal Muscle", Annals New York Academy of Science, 1993, vol. 707, pp. 417-420.

Squire, S., et al., "Prevention of pathology in mdx mice by expression of utrophin: analysis using an inducible transgenic expression system", Human Molecular Genetics, 2002. vol. 11, No. 26, pp. 3333-3344.

Steinhardt, Richard A., "Cardiology: rips repaired", Nature. Aug. 18, 2005, vol. 436, No. 7053, p. 925.

Straub, Volker, et al., "Muscular dystrophies and the dystrophin-glycoprotein complex", Current Opinion in Neurology, 1997, vol. 10, pp. 168-175.

Takahashi, Masaya, et al., "Effects of ACE inhibitor and AT1 blocker on dystrophin-related proteins and calpain in failing heart", Cardiovascular Research, 2005, vol. 65, pp. 356-365.

Torrente, Yvan, et al., "Human circulating AC133+ stem cells restore dystrophin expression and ameliorate function in dystrophic skeletal muscle", The Journal of Clinical Investigation, Jul. 2004, vol. 114, No. 2, pp. 182-195.

Toth, K., et al., "The effect of RheothRx Injection on the hemorheological parameters in patients with acute myocardial infraction", Clinical Hemorheology and Microcirculation, 1997, vol. 17, No. 2, pp. 117-125.

Townsend, DeWayne, et al., "Cardiomyopathy of Duchenne muscular dystrophy: pathogenesis and prospect of membrane sealants as a new therapeutic approach", Expert Review of Cardiovascular Therapy, Jan. 2007, vol. 5, No. 1, pp. 99-109.

Vanderbrouck, Clarisse, et al., "Involvement of TRPC in the abnormal calcium influx observed in Dystrophic (mdx) mouse skeletal muscle fibers", Journal of Cell Biology, Sep. 16, 2002, vol. 158, No. 6, pp. 1089-1096.

Verburg, Esther, et al., "Disruption of excitation-contraction coupling and titin by endogenous Ca2+-activated proteases in toad muscle fibers", J Phsiol, 2005, vol. 564, No. 3, pp. 775-789.

Wu, Guohui, et al., "Lipid Corralling and Poloxamer Squeeze-Out in Membranes", Physical Review Letters, 2004, vol. 93, No. 2, 028101.1-028101.4.

Yasuda, Soichiro, et al., "Dystrophic heart failure blocked by membrane sealant poloxamer", Nature, Nature Publishing Group, London, UK, Aug. 18, 2005, vol. 436, No. 7053, pp. 1025-1029.

Yasuda, So-ichiro, et al., "Membrane Sealant Poloxamer 188 Corrects the Primary Defect Caused by Dystrophin Deficiency in Single Cardiac Myocytes from Mdx Mice", Circulation, Oct. 2004, vol. 110, No. 17, p. 135.

Yeung, Ella W., et al., "Effects of stretched-activated channel blockers on [Ca2+]i and muscle damage in the mdx mouse", J Physiol, 2005, vol. 562, No. 2, pp. 367-380.

Yusuf, S., et al., "Effects of RheothRx on Mortality, Morbidity, Left Ventricular Function, and Infarct Size in Patients With Acute Myocardial Infarction", Collaborative Organization for RheothRx Evaluation (CORE), 1996, pp. 192-201.

Zile, Michael R., et al., "New Concepts in Diastolic Dysfunction and Diastolic Heart Failure: Part II: Casual Mechanisms and Treatment", Circulation, 2002, vol. 105, pp. 1503-1508.

Canadian Patent Application No. 2,599,219 Office Action dated Jul. 16, 2009.

EP Examination Report, EP Patent Application No. 06 736 222.8 dated Jan. 27, 2010.

EP Supplemental Search Report, EP Patent Application No. 06 736 222.8 dated Sep. 29, 2008.

Examiner's Report, Australian Patent Application No. 2006216420 dated Feb, 27, 2009.

International Search Report for PCT/US2006/006862 dated Aug. 29, 2006.

International Search Report for PCT/US2007/017182 dated Dec, 17, 2008.

International Search Report for PCT/US2008/004437 dated Jan. 13, 2009.

International Search Report for PCT/US2008/013728 dated Oct. 19, 2009.

International Search Report for PCT/US2008/087185 dated Jul. 29, 2009.

* cited by examiner

Changes in LVEF (percent) in severe heart failure animals over time, after treatment with P188 8 weeks after MI. CHF + P188/2 h, LVEF after 2 hours, CHF + P188/24 h, LVEF after 24 hours, CHF + P188/48 h, LVEF after 48 hours. Data are mean ± SE. N = 8. * P < 0.05 vs. all other groups.

Changes in LV Fractional Shortening (FS) in severe heart failure animals over time, after treatment with P188 (8 weeks after MI). CHF + P188/2 h: FS after 2 hours, CHF + P188/24 h: FS after 24 hours, CHF + P188/48 h:
FS after 48 hours. * $P < 0.05$ vs all groups, ** $P < 0.05$ vs P188/2 h and P188/48 h
Data are mean ± SE. N = 8.

LV End Diastolic Diameter (cm) in moderate-severe heart failure animals, treated with ranging doses of P188, 8 weeks after MI.
Data are mean ± SE. N = 4 for sham, 6 for CHF, 6 for 1.5 and (460 mg/kg), 11 for 0.46, 4.6 and 15.3 mg/kg. * P < 0.05 vs all groups.

LVEDP (mmHg) in Sham, heart failure animals untreated (CHF) heart failure treated with ranging dosages (0.46,4.6, 15.3 and 460 mg/kg)
* $P < 0.05$ vs all groups; ** $P < 0.05$ vs all groups, τ $P < 0.05$ vs all groups and ε $P < 0.05$ vs all groups. Data are mean ± SE, N = 4 for sham, 6 for CHF, 4 for 460, 6 for 1.5, and 11 for (0.46, 4.6 and 15.3).

LV Dimension in Systole (LVDs) in Moderate-Severe Heart Failure animals, treated with ranging doses of P188 8 weeks after MI.
Data are mean ± SE. * P <0.05 all groups.
N = 4 for sham, 6 for CHF, 4 for CHF (460 mg/kg),
N = 11 for (0.46, 4.6 and 15.3 mg/kg) and N = 6 for 1.5 mg/kg.

LVEF (percent) in Moderate-Severe Heart Failure animals, treated with ranging dosages of P188, 8 weeks after MI.
Data are mean ± SE. N = 4 for sham, 6 CHF, 4 (460 mg/kg), 6 (1.5 mg/kg) and 11 for 0.46, and 4.6 and 15.3 mg/kg.  **P < 0.05 vs all groups.

COMPOSITIONS AND METHODS FOR THE TREATMENT OF HEART FAILURE

CROSS REFERENCE

This application is a U.S. national phase application of PCT/US2008/004437, which was filed Apr. 4, 2008, and claims priority to U.S. application Ser. No. 60/922,047, filed on Apr. 5, 2007, the content of which is incorporated herein by reference in its entirety.

TECHNICAL FIELD

This invention relates generally to compositions and methods for treating heart failure. More specifically, the invention relates to a pharmaceutical composition for the treatment of heart failure that can be administered intermittently and has a continuous therapeutic effect.

BACKGROUND OF THE INVENTION

Heart failure (HF) is a pathological condition in which the heart is unable to pump blood at a rate required for normal metabolism and physical activity. Frequently, the exact causes of HF (particularly chronic HF) are unknown, but may be one or more of hypertension, myocardial injury, ischemic heart disease, cardiac valve abnormalities, coronary artery diseases, and abnormal electrical conduction within the heart. Alone or in combination, these conditions cause an increased chronic load on the heart which triggers three major compensatory mechanisms: the adrenergic system, the renin-angiotensin-aldosterone system, and ventricular hypertrophy. Although these mechanisms allow the heart to adapt and maintain adequate cardiac output, over time, they also bring about deleterious effects on the heart and cardiovascular system. These deleterious effects include cardiac myocyte hypertrophy leading to wall thickening and reduced contractility, elevated cytosolic calcium, causing impaired myocardial relaxation, vasoconstriction and aldosterone-induced salt and water retention, both of which may cause hypertension and additional load on the heart.

In current medical practice, patients are treated with one or more drugs that reduce stress on the heart. These drugs include vasodilators, diuretics, angiotensin receptor blockers, and beta-blockers. In combination with a healthy life style, these drug regimens improve symptoms and quality of life for the patient. Nevertheless, the pathophysiological changes in the heart progress over time causing debilitation of the heart and decreasing mobility and declining quality of life for the patient.

Poloxamer 188 ("P-188" or "P188") has been shown to improve cardiac output and reverse the heart failure associated with muscular dystrophy. Cardiac muscle cells exhibited a contractile defect that resulted from sustained high levels of cytosolic calcium. P-188, when added to an in vitro cardiac muscle preparation, appeared to seal tears in the muscle cell membrane, and thereby prevent an influx of calcium and allow cells to normalize their calcium levels. All of these affects of P-188 on cardiac muscle cells were observed in vitro, by placing the cell in a solution containing a fairly high concentration of P-188. Following exposure to P-188 treatment, heart muscle exhibited an improved ability to relax (improved diastolic function) and increased cardiac output. Furthermore, it is unknown whether these results are applicable to heart failure other than that associated with muscular dystrophy.

It would be desirable, to provide a treatment for heart failure that would slow or reverse the pathophysiological changes of the cardiac muscle tissue and could be administered intermittently but have a continuous therapeutic effect. Such a treatment would overcome many of the limitations and disadvantages inherent in the presently available treatments described above.

SUMMARY OF THE INVENTION

In one aspect, the present invention relates to a therapeutic composition which includes an aqueous buffer, and a therapeutic agent that improves the functioning of a diseased heart by decreasing left ventricular end-diastolic pressure or increasing left ventricular ejection without substantially affecting the blood pressure or heart rate.

As used herein, the term "significantly affecting the blood pressure or heart rate" refers to statistically significant deviation from the blood pressure or heart rate before the composition of this invention is administered. In general, a change that is not statistically significant is small enough that it can be ignored.

In some embodiments, the therapeutic agent improves the functioning of a diseased heart by decreasing left ventricular end-diastolic pressure without substantially affecting the blood pressure or heart rate.

In some embodiments, the therapeutic agent improves the functioning of a diseased heart by increasing left ventricular ejection without substantially affecting the blood pressure or heart rate.

In some embodiments, the therapeutic agent that improves the functioning of a diseased heart by decreasing left ventricular end-diastolic pressure and simultaneously increasing left ventricular ejection without substantially affecting the blood pressure or heart rate.

In some embodiments, the therapeutic composition improves the functioning of the diseased heart continuously for at least 24 hours (e.g., at least 48 hours, at least 7 days, or at least one month) following each administration of the therapeutic composition.

In some embodiments, the therapeutic agent contained in the therapeutic composition improves the functioning of a diseased heart independently of its concentration in the blood for at least 24 hours (e.g., at least 48 hours, at least 7 days, or at least one month) following each single administration of the therapeutic composition.

In some embodiments, the therapeutic agent is a polyoxyalkylene block copolymer. In some other embodiments, the therapeutic agent has a molecular weight in the range of 3,000 to 18,000. In some embodiments, the therapeutic agent is a poloxamer or poloxamine (e.g., Poloxamer 188, Poloxamer 407, Poloxamer 338, or Poloxamine 1107).

In some embodiments, the therapeutic composition is injectable or infusible.

In some embodiments, the disease of the heart is heart failure, e.g., chronic heart failure (such as ischemic heart failure) or acute heart failure.

Another aspect of this invention relates to a method for treating or ameliorating heart failure in a patient. The method includes administering to the patient a therapeutic composition comprising an aqueous buffer, and a therapeutic agent that improves the functioning of a diseased heart by decreasing left ventricular end-diastolic pressure or increasing left ventricular ejection without affecting the blood pressure or heart rate.

In some embodiments, the therapeutic composition used for treating or ameliorating heart failure improves the functioning of the diseased heart continuously for at least 24 hours (e.g., at least 48 hours, at least 7 days, or at least one month) following each administration of the therapeutic composition.

In some embodiments, the therapeutic agent contained in the therapeutic composition for preventing heart failure improves the functioning of a diseased heart independently of its concentration in the blood for at least 24 hours (e.g., at least 48 hours, at least 7 days, or at least one month) following each single administration of the therapeutic composition.

In some embodiments, the therapeutic agent contained in the therapeutic composition is a polyoxyalkylene block copolymer. In some other embodiments, the therapeutic agent has a molecular weight in the range of 3,000 to 18,000. In some embodiments, the therapeutic agent is a poloxamer or poloxamine (e.g., Poloxamer 188, Poloxamer 407, Poloxamer 338, or Poloxamine 1107).

The therapeutic compositions of this invention can be used together with therapeutic compositions useful for treating cardio or heart diseases, e.g., hypertension or congestive heart failure. Accordingly, the therapeutic compositions of this invention can also include compounds useful for treating such cardio or heart diseases.

As such, in some embodiments, a composition of this invention can further include an agent selected from the group consisting of angiotensin converting enzyme (ACE) inhibitors, angiotensin II receptor blockers (ARBs), beta-blockers, diuretics, digoxin, and anti-arrhythmic drugs. Examples of ACE inhibitors suitable for the compositions of this invention include, but are not limited to, captopril, benazepril, enalapril, lisinopril, fosinopril, ramipril, perindopril, quinapril, moexipril, and trandolapril. Examples of ARBs suitable for this invention include losartan, candesartan, irbesartan, and valsartan. Examples of beta-blockers suitable for the compositions of this invention include, but are not limited to, alprenolol, carteolol, levobunolol, mepindolol, metipranolol, nadolol, oxprenolol, penbutolol, pindolol, propranolol, sotalol, timolol, acebutolol, atenolol, betaxolol, bisoprolol, esmolol, metoprolol, nebivolol, carvedilol, celiprolol, labetalol, and butaxamine. Examples of diuretics suitable for this invention include, but are not limited to, calcium chloride, ammonium chloride, amphotericin B, lithium citrate, Goldenrod, Juniper, dopamine, acetazolamide, dorzolamide, bumetanide, ethacrynic acid, furosemide, torsemide, glucose, mannitol, amiloride, spironolactone, triamterene, bendroflumethiazide, hydrochlorothiazide, caffeine, and theophylline. Examples of anti-arrhythmic drugs suitable for this invention include, but are not limited to, disopyramide, procainamide, quinidine, lidocaine, phenyloin, flecamide, propafenone, propranolol, timolol, metoprolol, sotalol, atenolol, amiodarone, sotalol, bretylium, verapamil, and diltiazem.

In some embodiments, the therapeutic composition is injectable or infusible for treating or ameliorating heart failure.

In some embodiments, the disease of the heart to be treated or ameliorated is heart failure, e.g., chronic heart failure (such as ischemic heart failure) or acute heart failure.

Also within the scope of this invention are methods for treating, ameliorating, or preventing heart failure in a subject. The method includes administering to the patient a therapeutic composition comprising an aqueous buffer, and a therapeutic agent that improves the functioning of a diseased heart by decreasing left ventricular end-diastolic pressure or increasing left ventricular ejection, without substantially affecting the blood pressure or heart rate.

In some embodiments, the methods of this invention improve the functioning of a diseased heart by decreasing left ventricular end-diastolic pressure without substantially affecting the blood pressure or heart rate.

In some embodiments, the methods of this invention improve the functioning of a diseased heart by increasing left ventricular ejection without substantially affecting the blood pressure or heart rate.

In some embodiments, the methods of this invention improve the functioning of a diseased heart by decreasing left ventricular end-diastolic pressure and simultaneously increasing left ventricular ejection without substantially affecting the blood pressure or heart rate.

In some embodiments, the methods of this invention improve the functioning of the heart continuously for at least 24 hours (e.g., at least 48 hours, at least 7 days, or at least one month) following each administration of the therapeutic composition.

In some embodiments, the therapeutic agent contained in the compositions of this invention or used for the methods of this invention improves the functioning of a diseased heart independently of its concentration in the blood for at least 24 hours (e.g., at least 48 hours, at least 7 days, or at least one month) following each single administration of the therapeutic composition.

In some embodiments, the therapeutic agent used for the methods of this invention is a polyoxyalkylene block copolymer. In some other embodiments, the therapeutic agent has a molecular weight in the range of 3,000 to 18,000. In some other embodiments, the therapeutic agent is a poloxamer or poloxamine (e.g., Poloxamer 188, Poloxamer 407, Poloxamer 338, or Poloxamine 1107).

In some embodiments, the therapeutic agent used for the methods of this invention is injectable or infusible for treating, ameliorating, or preventing heart failure.

In some embodiments, the disease of the heart to be treated, ameliorated, or prevented by the methods of this invention is heart failure, e.g., chronic heart failure (such as ischemic heart failure) or acute heart failure.

The methods of this invention can be used together with other methods useful for treating cardio or heart diseases, e.g., hypertension or congestive heart failure. Accordingly, the methods of this invention can also include administering compounds useful for treating such cardio or heart diseases.

As such, in some embodiments, the methods of this inventions include administering the therapeutic agent to the patient in the amount of 0.15 mg/kg to about 480 mg/kg, e.g., about 460 mg/kg, about 250 mg/kg, about 150 mg/kg, about 15.3 mg/kg, about 4.6 mg/kg, about 1.5 mg/kg, or about 0.46 mg/kg.

In some further embodiments, the methods of this invention further include administering an agent selected from the group consisting of angiotensin converting enzyme (ACE) inhibitors, angiotensin II receptor blockers (ARBs), beta-blockers, diuretics, digoxin, and anti-arrhythmic drugs. Examples of ACE inhibitors suitable for the compositions of this invention include, but are not limited to, captopril, benazepril, enalapril, lisinopril, fosinopril, ramipril, perindopril, quinapril, moexipril, and trandolapril. Examples of ARBs suitable for this invention include, but are not limited to, losartan, candesartan, irbesartan, and valsartan. Examples of beta-blockers suitable for the compositions of this invention include, but are not limited to, alprenolol, carteolol, levobunolol, mepindolol, metipranolol, nadolol, oxprenolol, penbutolol, pindolol, propranolol, sotalol, timolol, acebutolol, atenolol, betaxolol, bisoprolol, esmolol, metoprolol, nebivolol, carvedilol, celiprolol, labetalol, and butaxamine. Examples of diuretics suitable for this invention include, but are not limited to, calcium chloride, ammonium chloride, amphotericin B, lithium citrate, Goldenrod, Juniper, dopamine, acetazolamide, dorzolamide, bumetanide, ethacrynic acid, furosemide, torsemide, glucose, mannitol, amiloride, spironolactone, triamterene, bendroflumethiazide, hydrochlorothiazide, caffeine, and theophylline. Examples of anti-arrhythmic drugs suitable for this invention include, but are not limited to, disopyramide, procainamide, quinidine, lidocaine, phenyloin, flecamide, propafenone, propranolol, timolol, metoprolol, sotalol, atenolol, amiodarone, sotalol, bretylium, verapamil, and diltiazem.

DETAILED DESCRIPTION OF THE INVENTION

Compositions of this Invention

Figure 1:
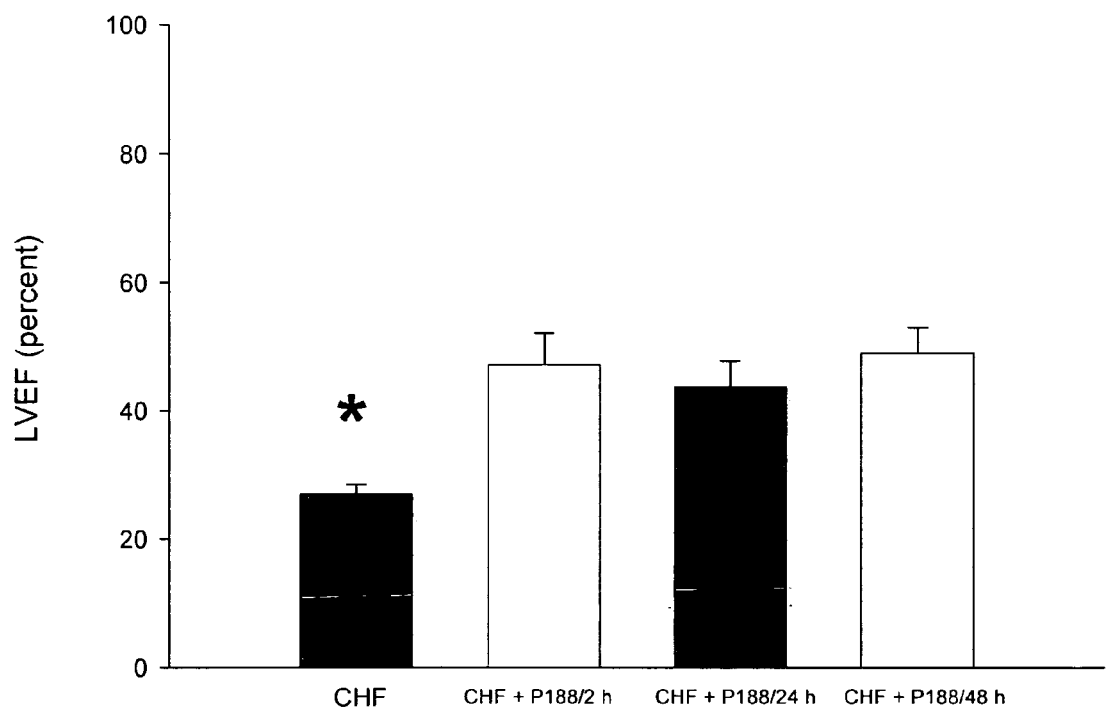
FIG. 1 shows the effect of P-188 on left ventricular ejection fraction in severe heart failure animals.

In one aspect, the present invention provides therapeutic compositions each of which includes an aqueous buffer, and a therapeutic agent that improves the functioning of a diseased heart by decreasing left ventricular end-diastolic pressure and simultaneously increasing left ventricular ejection without affecting the blood pressure or heart rate. These compositions have a physiologically acceptable pH, e.g., in the range of 4.5 to 7.5.

Suitable therapeutic agents include polyoxyalkylene block copolymer (e.g., those with a molecular weight in the range of 3,000 to 18,000). Examples of the polyoxyalkylene block copolymers include Poloxamers and Poloxamines.

Poloxamers are a series of polyoxyalkylene block copolymers having the general structure:

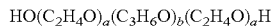

in which b is at least 15. The average molecular weights of the poloxamers range from about 1,000 to greater than 16,000 daltons. For example, Poloxamer 188 comprises a polyoxypropylene center block (with about 30 repeating units) flanked on either end by polyoxyethylene segments (each having about 75 repeating units) and has an average molecular weight of approximately 8,300. Poloxamer 407 comprises a polyoxypropylene center block (with about 67 repeating units) flanked on either end by polyoxyethylene segments (each having about 98 repeating units) and has an average molecular weight of approximately 11,500. Poloxamer 338 comprises a polyoxypropylene center block (with about 54 repeating units) flanked on either end by polyoxyethylene segments (each having about 128 repeating units) and has an average molecular weight of approximately 14,000.

Poloxamers can be prepared by methods known in the art for synthesizing block copolymers. For instance, the preparation of a poloxamer comprises synthesizing the center block and then capping the ends of the enter block with two polymer blocks. Specifically, the hydrophobic center block can be synthesized, e.g., in a base catalyzed ether condensation reaction using propylene glycol as the initiator and sequentially adding propylene oxide under an inert, anhydrous atmosphere, at elevated temperature and pressure. Upon reaching the desired molecular weight of the center block, the propylene oxide reactant is replaced by ethylene oxide. The polymer is then extended by the addition of ethylene oxide to form a hydrophilic segment of polyoxyethylene at each end of the polyoxypropylene block. Finally, the reaction is terminated by neutralization of the catalyst with an acid. More than thirty different poloxamers have been synthesized which range in molecular weight from 1,000 to 15,000. The polyoxyethylene content of the molecule may vary from 10% to 90% of the weight of the molecule. See, e.g., Reeve, L. E., "The Poloxamers: Their Chemistry and Medical Applications," pp. 231-249 in Handbook of Biodegradable Polymers, Eds. Domb, Kost and Wiseman, Harwood Academic Publishers (1997). Understandably, one can control the number of repeating propylene oxide or ethylene oxide units, and thus the length and weight of each of the poly(ethyleneoxide) and poly(propyleneoxide) blocks by changing the polymerization condition and time, or even the method. Specific examples of synthesis and characterization of poloxamers can be found in public literature and patent database. See, e.g., U.S. Pat. Nos. 6,977,045, 6,761,824, 5,811,080, 5,990,241, 6,359,014, 6,448,371, 6,747,064, 6,933,286, 5,567,859, RE 37,285, RE 36,665, RE 38,558, etc.

Poloxamines are four-branched block polyoxyalkylene block copolymers of poly(ethyleneoxide) and poly(propyleneoxide) having the general structure:

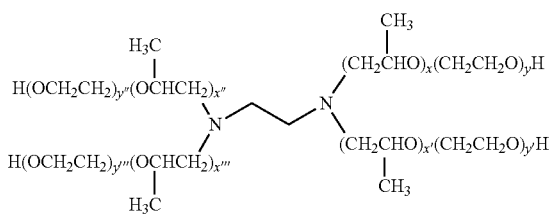

Poloxamine 1107, for example, has an average molecular weight of 15,400, and non-ionic surfactant properties. It has been used as a cellular membrane sealant, e.g., for repairing radiopermeabilized erythrocyte membranes.

Poloxamers and poloxamines are freely soluble in water, and are soluble in polar solvents. The Poloxamers are liquids, pastes or solids, depending largely on their polyoxyethylene to polyoxypropylene ratio and, secondarily, on their total molecular weight. In general, poloxamers having an average molecular weight of 3,000 or less are liquids if their polyoxyethylene content is not more than 50%. Poloxamers with molecular weights between 3,000 and 5,000 are liquids only if their polyoxyethylene content is 20% or less. Pastes range in molecular weight from 3,300 to 6,600 with a polyoxyethylene content between 30% and 50%. Solid poloxamers are the largest, having molecular weights of 5,000 to 15,000 and polyoxyethylene content of 70% or greater.

As such, the Poloxamers and poloxamines (e.g., Poloxamer 188, Poloxamer 338, Poloxamer 407, or Poloxamine 1107) can be dissolved into water or an aqueous buffer to the desired concentration, e.g., 5-300 g/L, to give a polymer solution that can be later used to prepare a composition of this invention or practice the methods of this invention.

The compositions of this invention also include an aqueous buffer. As used herein, the term "aqueous buffer" refers to a water solution which resists change in hydronium ion and the hydroxide ion concentration (and consequent pH) upon addition of small amounts of acid or base, or upon dilution. Buffer solutions consist of a weak acid and its conjugate base (more common) or a weak base and its conjugate acid (less common). The buffer can be prepared by methods well known in the art with the appropriate buffering agents to give the desired pH value. Examples of the suitable buffering agents include hydrochloric acid, lactic acid, acetic acid, citric acid, malic acid, maleic acid, pyruvic acid, succinic acid, tris-hydroxymethylaminomethane, sodium hydroxide, sodium bicarbonate, phosphoric acid, sodium phosphate, and other biologically acceptable buffering agents. Of course, aqueous buffers are readily available commercially and they can be used in preparation of the compositions of this invention without further treatment.

Uses of the Compositions of this Invention

As used herein, the term "heart failure" refers to a condition that can result from any structural or functional cardiac disorder that impairs the ability of the heart to fill with or pump a sufficient amount of blood throughout the body. As used herein, the term "chronic heart failure" refers to a sustained inability of the heart to pump blood forward at a sufficient rate to meet metabolic demands. Examples of chronic heart failure include systolic dysfunction, diastolic dysfunction, right-sided heart failure, and ischemic heart failure. As used herein, the term "acute heart failure" refers to acute decompensation episodes in chronic heart failure patients.

The compositions of this invention can be used for treating or ameliorating a diseased heart in a patient or to prevent certain heart disease in a subject (e.g., a human patient or animal). The disease can be heart failure, e.g., chronic heart failure (such as ischemic heart failure) or acute heart failure.

For instance, a composition of this invention can be injected or infused into the blood vessel of a patient (or a subject) with a diseased heart and in need of the treatment. The therapeutic agent in the composition (e.g., a poloxamer or poloxamine) then circulates into the heart. Not wishing to be bound by this theory, the therapeutic agent contained in the compositions of this invention may decrease the contractile stress of the heart muscle, and in a condition of low membrane dystrophin levels, may even decrease membrane damage enough to allow the heart to repair itself. In other words, the therapeutic composition may aid in the repair of membrane damage in a diseased heart without the need of a surgical procedure to unload the heart.

The efficacy of the compositions of this invention in treating, ameliorating, or even preventing heart disease can be determined by methods known in the art, e.g., by measuring the blood flow rate or volume in vitro or in an animal model or the pharmacokinetics of the therapeutic agent in the composition. See, e.g., Grindel J. M. et al., *Biopharm. Drugs Dispos.*, 2002, 23: 87-103.

One specific example to ways to determine the efficacy of the compositions or methods of this invention is to measure the ejection fraction, specifically the left ventricular ejection fraction (LVEF). Ejection fraction refers to the fraction of blood pumped out of a ventricle with each heart beat. By definition, the volume of blood within a ventricle immediately before a contraction is known as the end-diastolic volume. Similarly, the volume of blood left in a ventricle at the end of contraction is end-systolic volume. The difference between end-diastolic and end-systolic volumes is the stroke volume, the volume of blood ejected with each beat. Ejection fraction is the fraction of the end-diastolic volume that is ejected with each beat; that is, it is stroke volume (SV) divided by end-diastolic volume (EDV).

Ejection fraction is commonly measured by echocardiography, in which the volumes of the heart's chambers are measured during the cardiac cycle. Ejection fraction can then be obtained by dividing stroke volume by end-diastolic volume as described above.

Other methods of measuring ejection fraction include cardiac MRI, fast scan cardiac computed axial tomography (CT) imaging, and ventriculography. The historical gold standard for the measurement of ejection fraction is ventriculography.

The shortening fraction (or "fractional shortening") is a slightly different way of measuring left ventricle performance. Instead of measuring and ratio-ing blood volumes, the shortening fraction measures and ratios the change in the diameter of the left ventricle between the contracted and relaxed states:

$$\frac{LV \text{ end-diastolic diameter} - LV \text{ end-systolic diameter}}{LV \text{ end-diastolic diameter}}.$$

Other methods for determining the efficacy of the compositions or methods of this invention include the left ventricular end-diastolic diameter (or dimension) or the left ventricular end-systolic diameter (or dimension), which measures the actual ventricle's diameter (or dimension) and correlates to the performance of the left ventricle. Additionally, the efficacy can be determined by measuring the left ventricular end-diastolic pressure (LVEDP) or left ventricular end-diastolic volume (LVEDV), e.g., with a pressure or pressure/volume catheter inserted directly into the left ventricle.

Set forth below are some examples that illustrate use of the compositions of this invention. These examples are intended only to be illustrative of, not in any way limiting, this invention.

All publications cited herein are incorporated by reference in their entireties.

EXAMPLE 1

Effect on Heart Failure

In a rat myocardial infarction (MI) heart failure model, the left anterior descending coronary artery (LAD) is tied off to produce an infarction of greater than 40%. The rats become stable after 1 to 3 weeks and in 3 weeks exhibit significant left ventricular (LV) dysfunction. 8-weeks post-MI rats are used due to their loss of dystrophin. Control groups include untreated heart failure rats, sham-operated animals where the LAD was exposed but not tied off as well as rats that did not undergo the surgery (normal).

On the day of treatment, rats were infused with P-188 at 460 mg/kg over a 30 minute period and the heart was catheterized and hemodynamics was monitored over a 4-hr period.

Figure 2:
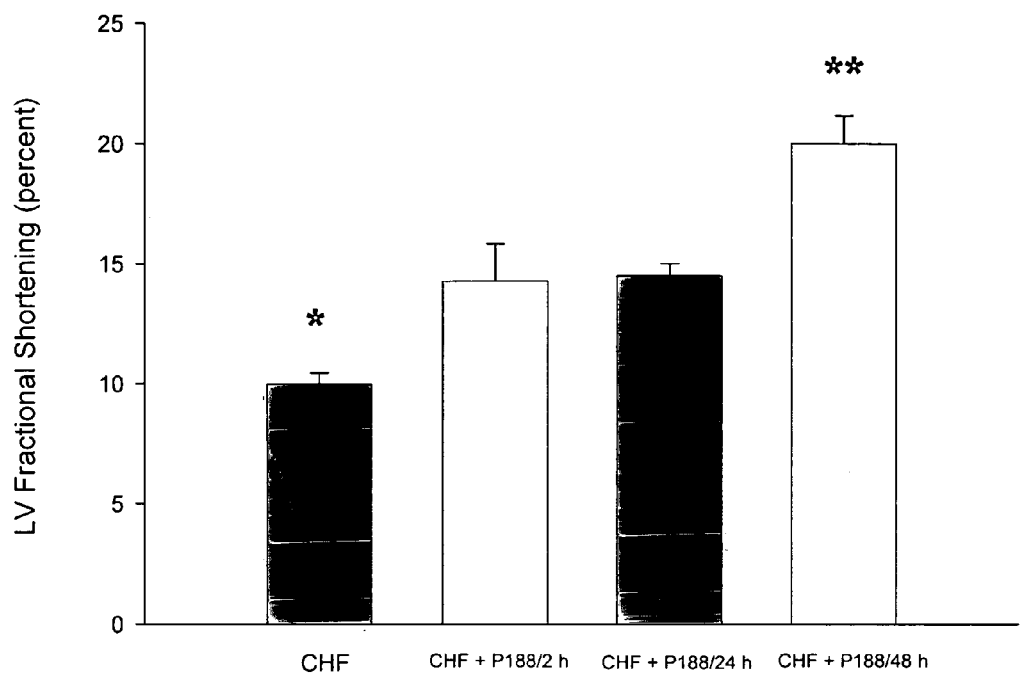
FIG. 2 shows the effect of P-188 on left ventricular fractional shortening in severe heart failure animals.
Figure 4:
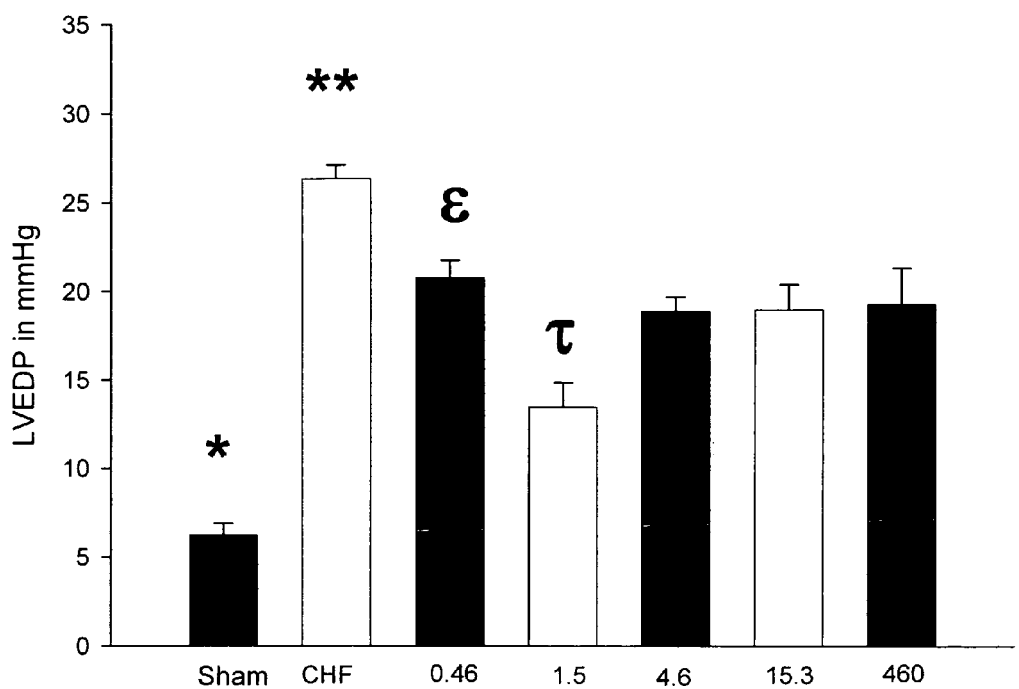
FIG. 4 shows the effect of P-188 on left ventricular end-diastolic pressure in heart failure animals at different dosages.

Compared with untreated MI rats, P-188 treatment caused a significant decrease in left ventricular end-diastolic pressure (LVEDP), as shown in FIG. 4. As shown in FIG. 1, at the dosage of 460 mg/kg, administration of P-188 also caused a significant increase in left ventricular ejection fraction (LVEF), a measurement that indicates the ability of the heart to empty its content during systole. Additionally, as shown in FIG. 2, it also caused a significant increase in left ventricular fractional shortening in severe heart failure rats. The heart rate (HR), left ventricular systolic pressure (LVSP), left ventricular isovolumic contraction (LV+dP/dt), and left ventricular end-systolic volume did not change significantly.

The results indicate that P-188 had an effect on cardiac hemodynamics. The approximate 25% increase in ejection fraction was clinically significant. Ejection fraction is the percent of end-diastolic volume that is ejected as the stroke volume and is a measurement of pump function. It can be influenced by blood pressure (afterload), the amount of blood returning to the heart (preload), volume of the heart chamber, and heart rate. Additionally, P-188 treatment did not affect heart rate (HR), and did not increase afterload because LVSP did not rise. Thus, it appears that P-188 had an effect on preload, which can be influenced by venous return of blood to the heart as well as the ability of the heart to relax. LVEDP, also influenced by these parameters, was decreased. Since a significant drop in venous return should be accompanied by a change in blood pressure, which was not seen with P-188, it is likely that the results indicate that P-188 increased the relaxation properties of the working heart.

EXAMPLE 2

Duration of Action

HF rats were infused with a single dose of P-188 and monitored by echocardiography at 2, 24, and 48 hour post infusion. Blood samples were also taken to determine serum concentrations of the P-188.

As was indicated in Example 1 and shown in FIG. 1, treatment of rats with severe HF with P-188 at 460 mg/kg resulted in a significant increase in left ventricular ejection fraction at 2 hours and was maintained out to 48 hours of treatment. As shown in FIG. 2, left ventricular fractional shortening, the change in diameter of the LV chamber from end-diastole to end-systole divided by the LVED diameter, was increased significantly after P-188 at all time points, particularly with an increase of 50% at 2 and 24 hours and a nearly 100% increase at 48 hours. Left ventricular dimension in both diastole and systole were unchanged during the first 24 hours. These results indicate an increase in contractility in the P-188 treated hearts that was sustained or improved over the 48 hours of the study.

The results obtained in this study are consistent with P-188 having an affect on the relaxation properties of the left ventricle. An increase in LV compliance with a concomitant increase in preload, resulting in a stretching of the myofibrils would be expected to increase fractional shortening, contractility, and ejection fraction at 460 mg/kg. This is consistent with the decrease in LV end-diastolic pressure seen in Example 1. The half-life for plasma clearance in the rat has been reported to range from 4.9 to 8.0 hours.

EXAMPLE 3

Treatment at Different Doses

Rats with moderate or severe heart failure were treated with the compositions of this invention at 0.46 mg/kg, 1.5 mg/kg, 4.6 mg/kg, 15.3 mg/kg, and 460 mg/kg (amount of P-188/body weight of rats) over a 30-minute period. Also used in the same studies were a control group (CHF) and a Sham group. Neither of these groups received treatment but both represented an upper limit (CHF) and a lower limit (Sham) of the parameters being measured.

Figure 3:
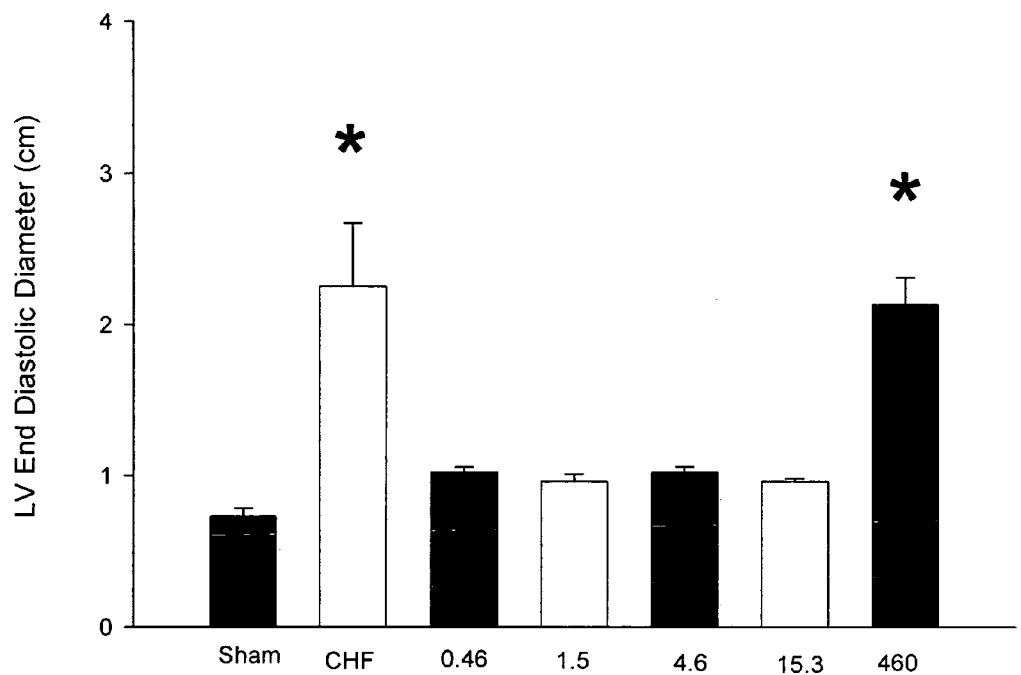
FIG. 3 shows the effect of P-188 on left ventricular end-diastolic diameter in heart failure animals at different dosages.

As shown in FIG. 3, treatment of P-188 at the dosages of 0.46-15.3 caused a significant decrease in the left ventricular end-diastolic pressure in moderate or severe heart failure rats. As shown in FIG. 4, all doses of P-188 lowered LVEDP compared with the untreated CHF rats. However, only the dosage of 1.5 mg/kg of P-188 caused an even more significant decrease in the left ventricular diastolic pressure, while the effects of other dosages were not as pronounced.

Figure 5:
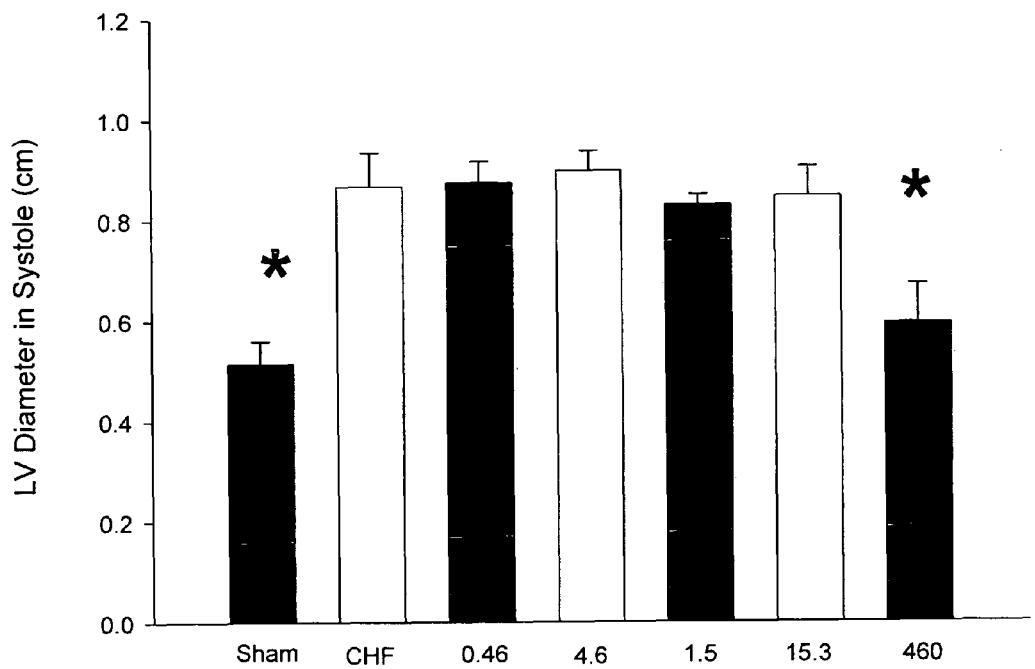
FIG. 5 shows the effect of P-188 on left ventricular end-systolic diameter in heart failure animals at different dosages.
Figure 6:
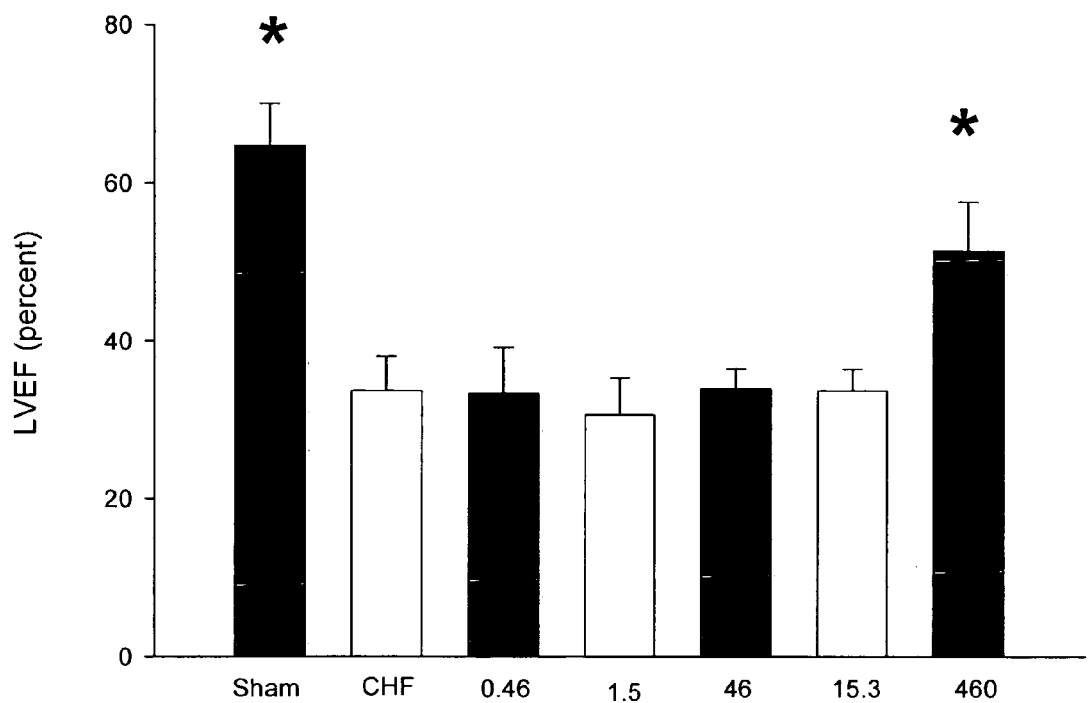
FIG. 6 shows the effect of P-188 on left ventricular ejection fraction in heart failure animals at different dosages.

By contrast, as shown in FIG. 5 and FIG. 6, the P-188 dosage of 460 mg/kg caused a significant decrease in the left ventricular systolic diameter of the treated rats and a significant increase in the left ventricular ejection fraction, while the other dosages did not have as much effect.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating or ameliorating heart failure in a subject having a diseased heart by decreasing left ventricular end-diastolic pressure or increasing left ventricular ejection fraction without substantially affecting the blood pressure or heart rate, comprising administering to the subject in need thereof a therapeutic composition comprising
   an aqueous buffer, and
   a therapeutic agent
   wherein the therapeutic agent is a poloxamer or poloxamine selected from the group consisting of Poloxamer 188, Poloxamer 338 or Poloxamine 1107, and
   wherein each dosage of the poloxamer or poloxamine ranges from 0.15 to about 15.3 mg/kg.

2. The method of claim 1, wherein the therapeutic composition improves the functioning of the diseased heart continuously for at least 24 hours following each administration of the therapeutic composition.

3. The method of claim 1, wherein the therapeutic agent improves the functioning of a diseased heart independently of its concentration in the blood for at least 24 hours following each single administration of the therapeutic composition.

4. The method of claim 1, wherein the therapeutic agent is Poloxamer 188.

5. The method of claim 1, wherein the heart failure is acute heart failure.

6. The method of claim 1, wherein the heart failure is chronic heart failure.

7. The method of claim 1, wherein the heart failure is ischemic heart failure.

8. The method of claim 1, wherein the therapeutic composition is administered by injection or infusion.

9. The method of claim 1, wherein the therapeutic agent in the composition is administered to the patient in the amount of about 15.3mg/kg.

10. The method of claim 1, wherein the therapeutic agent in the composition is administered to the patient in the amount of about 4.6mg/kg.

11. The method of claim 1, wherein the therapeutic agent in the composition is administered to the patient in the amount of about 1.5mg/kg.

12. The method of claim 1, wherein the therapeutic agent in the composition is administered to the patient in the amount of about 0.46mg/kg.

13. The method of claim 1, further comprising administering to the subject an agent selected from a group consisting of angiotensin converting enzyme (ACE) inhibitors, angiotensin II receptor blockers (ARBs), beta-blockers, diuretics, digoxin, and anti-arrhythmic drugs.

14. The method of claim 13, wherein the ACE inhibitors consist of captopril, benazepril, enalapril, lisinopril, fosinopril, ramipril, perindopril, quinapril, moexipril, and trandolapril; ARBs consist of losartan, candesartan, irbesartan, and valsartan; beta-blockers consist of alprenolol, carteolol, levobunolol, mepindolol, metipranolol, nadolol, oxprenolol, penbutolol, pindolol, propranolol, sotalol, timolol, acebutolol, atenolol, betaxolol, bisoprolol, esmolol, metoprolol, nebivolol, carvedilol, celiprolol, labetalol, and butaxamine; diuretics consist of calcium chloride, ammonium chloride, amphotericin B, lithium citrate, Goldenrod, Juniper, dopamine, acetazolamide, dorzolamide, bumetanide, ethacrynic acid, furosemide, torsemide, glucose, mannitol, amiloride, spironolactone, triamterene, bendroflumethiazide, hydrochlorothiazide, caffeine, and theophylline; anti-arrhythmic drugs consist of disopyramide, procainamide, quinidine, lidocaine, phenytoin, flecainide, propafenone, propranolol, timolol, metoprolol, sotalol, atenolol, amiodarone, sotalol, bretylium, verapamil, and diltiazem.

* * * * *